United States Patent
McGee, II (10) Patent No.: US 11,547,550 B2
(45) Date of Patent: Jan. 10, 2023

(54) PATELLAR TENDON GRAFT AND ANTERIOR CRUCIATE LIGAMENT (ACL) RECONSTRUCTION METHOD USING SUTURE TAPE AUGMENTATION

(71) Applicant: William R. McGee, II, Las Vegas, NV (US)

(72) Inventor: William R. McGee, II, Las Vegas, NV (US)

( * ) Notice: Subject to any disclaimer, the term of this patent is extended or adjusted under 35 U.S.C. 154(b) by 548 days.

(21) Appl. No.: 16/676,276

(22) Filed: Nov. 6, 2019

(65) Prior Publication Data

US 2020/0315771 A1    Oct. 8, 2020

Related U.S. Application Data

(60) Provisional application No. 62/756,298, filed on Nov. 6, 2018.

(51) Int. Cl.
| | | |
|---|---|---|
| *A61F 2/08* | (2006.01) | |
| *A61B 17/06* | (2006.01) | |
| *A61B 50/33* | (2016.01) | |
| *A61B 17/14* | (2006.01) | |
| *A61B 17/04* | (2006.01) | |

(Continued)

(52) U.S. Cl.
CPC ............ *A61F 2/08* (2013.01); *A61B 17/0467* (2013.01); *A61B 17/062* (2013.01); *A61B 17/06066* (2013.01); *A61B 17/06166* (2013.01); *A61B 17/142* (2016.11); *A61B 17/1604* (2013.01); *A61B 17/1615* (2013.01); *A61B 17/1635* (2013.01); *A61B 50/33* (2016.02); *A61B 2017/00867* (2013.01); *A61B 2050/314* (2016.02); *A61F 2002/0858* (2013.01)

(58) Field of Classification Search
CPC .... A61F 2/08; A61F 2002/0585; A61B 50/33; A61B 17/142; A61B 17/0467; A61B 17/06066; A61B 17/06166; A61B 17/062; A61B 17/1604; A61B 17/1615; A61B 17/1635; A61B 2050/314; A61B 2017/00867
USPC ...................................... 623/13.12
See application file for complete search history.

(56) References Cited

U.S. PATENT DOCUMENTS 7,901,455 B2 *   3/2011   Koob ..................... C07K 14/78
                                                    623/13.14
8,298,284 B2 *  10/2012   Cassani ..................... A61F 2/08
                                                    623/13.12

(Continued)

*Primary Examiner* — Jessica Weiss
(74) *Attorney, Agent, or Firm* — C. Brandon Browning; Maynard, Cooper & Gale, PC (57) ABSTRACT

The present disclosure generally pertains to methods and kits for preparing an ACL repair surgical implant, the method including drilling femoral and tibial bone plugs of a tendon graft to create medial to lateral holes, and passing a braided suture around the tendinous portion of the tibial end, through soft tissue, and out the tibial end. Next, an anterior to posterior femoral hole is drilled, and a flat-braided suture is passed through the femoral medial to lateral hole and, using a bent needle, passed through junctions of the femoral bone plug and the tendinous portion and out through junctions of the tibial bone plug and the tendinous portion on both sides of the graft. Ends of the flat-braided suture are crisscrossed through the medial to lateral tibial hole. A bone-to-bone fixation suture assembly is passed through the anterior to posterior femoral hole.

3 Claims, 10 Drawing Sheets

(51) Int. Cl.
*A61B 17/062* (2006.01)
*A61B 17/16* (2006.01)
A61B 50/30 (2016.01)
A61B 17/00 (2006.01)

(56) References Cited

U.S. PATENT DOCUMENTS

| | | | | |
|---|---|---|---|---|
| 9,216,077 | B2* | 12/2015 | Davis | A61L 17/08 |
| 2001/0018619 | A1* | 8/2001 | Enzerink | A61F 2/08 |
| | | | | 623/23.72 |
| 2020/0093481 | A1* | 3/2020 | Dooney, Jr. | A61L 17/06 |
| 2020/0315771 | A1* | 10/2020 | McGee, II | A61B 17/1615 |

* cited by examiner

PATELLAR TENDON GRAFT AND ANTERIOR CRUCIATE LIGAMENT (ACL) RECONSTRUCTION METHOD USING SUTURE TAPE AUGMENTATION

RELATED APPLICATIONS

This application claims priority to U.S. Provisional Application No. 62/756,298 filed on Nov. 6, 2018, titled "Patellar Tendon Graft And Anterior Cruciate Ligament (ACL) Reconstruction Method Using Suture Tape Augmentation," the entire contents of which are incorporated herein.

TECHNICAL FIELD

The present invention is directed to surgical devices, surgical kits, and methods of using same for the reconstruction of the anterior cruciate ligament using a suture tape modified patellar tendon graft.

BACKGROUND OF INVENTION

Anterior cruciate ligament, or ACL reconstruction is often necessary or recommended when the ACL is torn or otherwise injured. This ligament is a major ligament of the knee that stabilizes it during rotation and is located behind the patella, connecting the femur to the tibia. Injuries, such as sprains, partial-tears, or tears, may occur during activities that involve quick changes in direction, slowing, or stopping. ACL reconstruction allows the replacement of the torn ligament with substitute tissue, which is typically tendon tissue. Sources include autografts, which is tissue from the same patient in which the ACL is to be reconstructed, and allografts, which is tissue from a donor or cadaver.

In ACL reconstruction surgical procedures, the injured or torn ACL is first removed and the joint inspected for any further damage. Next, tunnels are made between the tibia and the knee joint and between the femur and the knee joint, serving as anchor point for the tendon graft. The graft is then inserted through each tunnel and secured at the tibia and femur using screws and bone anchors. The inserted graft then acts as a scaffold for further growth and strengthening, allowing the ACL to be reconstructed.

While the surgical technique aims to provide the patient with a functional ALC and to allow the patient to return to normal activities or sports, graft rupture and incomplete function remain significant challenges. Thus, reinforcement techniques for graft tissue have been devices to enhance graft stability. The present invention presents a technique for ACL reconstruction using a patellar tendon graft augmented with a cross linked suture tape. A cortical button is used for fixation on the femoral side, while either a button or interference screw plus suture anchor are used for the tibial side fixation. The graft preparation of this technique has, to our best knowledge, not been previously described, and constitutes a novel method for enhancing graft stability and strength.

SUMMARY OF THE INVENTION

The present invention is directed to a surgical kit, a surgical implant, and a method of preparing the surgical implant for the use in anterior cruciate ligament (ACL) reconstruction. In one aspect of the invention, there is provided a surgical kit including a patellar bone-tendon graft having a tibial end, a femoral end, a tendinous portion, a tibial bone plug, and a femoral bone plug. The surgical kit additionally includes a braided suture, a flat-braided suture, a straight needle, a bone-to-bone fixation suture, an interference screw, a bone anchor, a 9 mm oscillating saw blade, a rongeur, a needle driver, suture scissors, a 1.5 mm drill bit, and a drill. In some instances, the surgical kit is contained within a sterile package, the sterile package being selected from the group consisting of a sealed tray, a sealed bag, a sealed metal foil bag, a sealed plastic bag, a sealed plastic tray, a sealed metal tray, and a foil-sealed plastic or metal tray. In some instances, the patellar tendon graft is an autograft, while in other cases, the patellar tendon graft is an allograft.

According to another aspect of the present invention, there is provided a method of making a surgical implant. The method includes first providing a patellar bone-tendon graft having a tibial end, a femoral end, a tendinous portion, a tibial bone plug, and a femoral bone plug. Next, the femoral bone plug is shaped into a first cylinder and the tibial bone plug is shaped into a second cylinder. A medial to lateral drill hole is then drilled in each of the femoral bone plug and the tibial bone plug. The method further includes providing a braided suture in the form of a continuous loop and attached to a straight needle having a Nitinol loop, followed by securing the braided suture to the graft by passing the braided suture around the tendinous portion of the tibial end of the graft, making at least two passes with the straight needle and braided suture through the tendinous portion, and passing the straight needle through soft tissue on a posterior aspect of the tibial bone plug and out through the tibial end thereof which serves as a passing or shuttle structure. The straight needle is then detached from the braided suture while keeping the Nitinol loop intact, followed by placing the straight needle through the medial to lateral drill hole in the femoral bone plug and maintaining the straight needle in the medial to lateral drill hole as a reference. Next, an anterior to posterior hole is drilled in the femoral bone plug immediately beneath and perpendicular to the straight needle located in the medial to lateral drill hole, and a flat-braided suture is passed through the medial to lateral hole of the femoral bone plug using the straight needle as a shuttle.

After slightly bending the straight needle with a needle driver, a first end of the flat-braided suture is passed using the needle through a junction of the femoral bone plug and the tendinous portion on a first side of the graft and out through a junction of the tibial bone plug and the tendinous portion on the first side of the graft, with the needle extending parallel to fibers of the tendinous portion. A second end of the flat-braided suture is likewise passed using the needle through the junction of the femoral bone plug and the tendinous portion on a second side of the graft and out through the junction of the tibial bone plug and the tendinous portion on the second side of the graft, with the needle extending parallel to fibers of the tendinous portion. The first end of the flat-braided suture and the second end of the flat-braided suture are then passed through the medial to lateral drill hole in the tibial bone plug in a crisscross fashion. Finally, a bone-to-bone fixation suture assembly is passed through the anterior to posterior hole in the femoral bone plug and operatively coupling the bone-to-bone fixation suture assembly to the graft, thereby forming an interlocking loop between the flat-braided suture and the bone-to-bone fixation suture assembly.

In some instances, the patellar bon-tendon graft is an autograft. The autograft includes a portion of a patella tendon, a patellar bone region, and a tibial bone region in some embodiments, while in other embodiments, the autograft comprises a portion of the hamstring tendon. In some instances, the patellar tendon graft is an allograft. The disclosure includes a method of storing the surgical implant, including the steps of placing the surgical implant in a sterile package, the sterile package being selected from the group consisting of a sealed tray, a sealed bag, a sealed metal foil bag, a sealed plastic bag, a sealed plastic tray, a sealed metal tray, and a metal foil-sealed plastic or metal tray, followed by cooling the surgical implant. The storage method further includes freezing the surgical implant at −20±10° C. in some embodiments. The disclosure includes a method of transporting the surgical implant, including the step of placing the surgical implant in a sterile package, the sterile package being selected from the group consisting of a sealed tray, a sealed bag, a sealed metal foil bag, a sealed plastic bag, a sealed plastic tray, a sealed metal tray, and a metal foil-sealed plastic or metal tray. The transporting may further include freezing the surgical implant, placing the surgical implant in a transportable cooler, and transporting the surgical implant within the transportable cooler.

In yet another aspect of the present invention, there is provided a surgical implant including a patellar bone-tendon graft having a tibial end, a femoral end, a tendinous portion, a tibial bone plug, and a femoral bone plug, wherein the femoral bone plug is shaped into a first cylinder and the tibial bone plug is shaped into a second cylinder. The implant additionally includes a medial to lateral drill hole formed in each of the femoral bone plug and the tibial bone plug, and a braided suture provided in the form of a continuous loop and attached to a straight needle having a Nitinol loop, the braided suture in the form of a continuous loop secured to the graft by passing the braided suture around the tendinous portion of the tibial end of the graft, passing the braided suture through the tendinous portion, and passing the braided suture through soft tissue on a posterior aspect of the tibial bone plug and out through the tibial end thereof. The surgical implant further includes an anterior to posterior hole formed in the femoral bone plug immediately beneath the medial to lateral drill hole therein, a flat-braided suture passed through the medial to lateral hole of the femoral bone plug, a first end of the flat-braided suture passed through a junction of the femoral bone plug and the tendinous portion on a first side of the graft and out through the junction of the tibial bone plug and the tendinous portion on the first side of the graft, and a second end of the flat braided suture passed through the junction of the femoral bone plug and the tendinous portion on a second side of the graft and out through the junction of the tibial bone plug and the tendinous portion on the second side of the graft. The first end of the flat-braided suture and the second end of the flat-braided suture are passed through the medial to lateral drill hole in the tibial bone plug in a crisscross fashion. A bone-to-bone fixation suture assembly is also included and passed through the anterior to posterior hole in the femoral bone plug and operatively coupled to the graft, thereby forming an interlocking loop between the flat-braided suture and the bone-to-bone fixation suture assembly.

In some instances, the patellar bone-tendon graft is an autograft, while in other instances the patellar bone-tendon graft is an allograft. In some embodiments, the surgical implant is stored within a sterile package, the sterile package being selected from the group consisting of a sealed tray, a sealed bag, a sealed metal bag, a sealed plastic bag, a sealed plastic tray, a sealed metal tray, and a metal foil-sealed plastic or metal tray. The stored surgical implant is, in some instances, frozen at −20±10° C. In some embodiments, the surgical implant is included in a surgical kit, which may further include at least one interference screw and at least one bone anchor.

A further understanding of the nature and advantages of the present invention will be realized by reference to the remaining portions of the specification and the drawings.

BRIEF DESCRIPTION OF DRAWINGS

The present disclosure same can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION OF THE INVENTION

The present invention is generally directed to a surgical kit or surgical device for anterior cruciate ligament (ACL) reconstruction using an augmented patellar bone-tendon graft 10 and methods of reconstruction using same. The augmentation involves the use of structuring, flexible materials, such as suture tape, to strengthen patellar tendon graft 10 and improve graft stability following insertion in the patient. The preparation of patellar tendon graft 10 with cross-linked suture tape prior to graft placement has not been otherwise displayed, and constitutes a potential functional improvement over non-augmented grafts.

Figure 1:
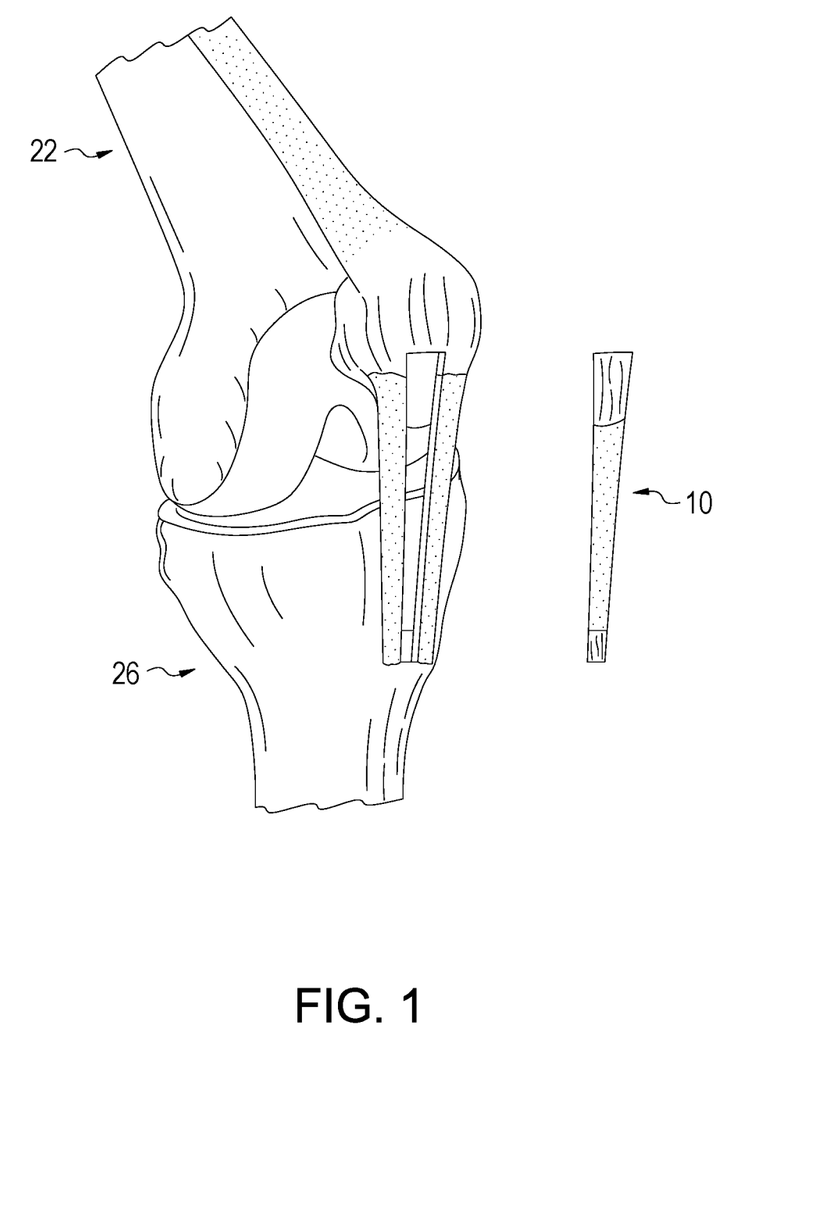
FIG. 1 is a perspective view of a kneecap from which a patellar bone-tendon graft has been removed for anterior cruciate ligament (ACL) surgery in accordance with the present invention.

Referring to FIG. 1, patellar tendon graft 10 is first harvested, either from the same patient to which ACL reconstruction will be performed or from another source, such as a cadaver. Thus, patellar tendon graft 10 is in some instances an autograft and in other instances an allograft. It is contemplated that the graft augmentation technique described herein may be used with grafts other than patellar tendon autografts and allografts including, for example, hamstring tendon grafts, quadriceps tendon grafts and Achilles tendon grafts. When an autograft is utilized for patellar tendon graft 10, it is harvested immediately prior to reconstruction. However, in embodiments not shown herein, an autograft patellar tendon graft 10 is harvested from the patient, prepared for insertion, and then stored for a period of time prior to insertion. When an allograft is utilized for patellar tendon graft 10, it is prepared prior to reconstruction surgery and either inserted immediately after preparation or stored for a period of time prior to reconstruction surgery. An allograft may be sterilely fabricated and sterilely packaged within a bag, tray or pouch for storage, transportation and later use. Such allografts can be made by a skilled technician in a laboratory, away from the operating room, and without any time constraints similar to those of augmenting an autograph in an operating room environment immediately before surgery. Exemplary packaging may include a plastic or metal tray having a peal-away metal foil or plastic lid for sealing the tray, a seamless plastic or metal foil bag or a sealed glass, plastic or metal bottle having a removable, screw-type lid. Other packaging means suitable for the sterile storage of patellar tendon graft 10 until reconstruction surgery are contemplated.

When patellar tendon graft 10 is stored, it is cooled or frozen at a temperature of approximately −20±10° C. The storage time varies according to application, transportation distance, and other circumstances related to patient care. For instance, patellar tendon graft may be stored at a cool temperature of approximately −20±10° C. for several hours, several days, or several months. In some instances, patellar tendon graft 10 may be stored for up to about 6 months at −20±10° C. For longer periods of storage, from several months to several years, patellar tendon graft 10 may be stored at a temperature ranging from approximately −40° C. to approximately −90° C. Transport of patellar tendon graft 10 may be under cooling conditions, such as in a transportable cooler or similar insulated cooling device. When transported, patellar tendon graft 10 may be stored with a cooling material, such as ice, and maintained in sterile conditions.

To harvest patellar tendon graft 10, a patient is placed supine on a table or flat surface. A lateral post, such as the Shutt Universal Stress Post (Conmed, Inc.), is positioned approximately 3-4 finger breaths superior to the patella. A sandbag is taped to the bed so that the foot can rest against it with the knee at 90 degrees of flexion when harvesting an autograft. If an allograft is being used, no sandbag is necessary. A tourniquet is placed on the upper thigh and inflated to approximately 250 mm Hg. The leg is prepped and draped in sterile fashion, as is known in the art.

For an autograft, an anterior midline incision is made from the inferior pole of the patella to the tibial tubercle. 13×18 mm Smillie retractors with a down curve are used for exposure of the tendon. The central third of the patella is harvested. Preferably, an approximately 10 or 11 mm wide portion of the middle of the tendon is taken. Using a 9 mm oscillating saw, an 18 mm bone plug is taken from each of the patella and the tibia. An 8 mm mini Lambotte osteotome is used on the patella and a curved ¼ inch osteotome is used on the tibia. The graft is then prepared on a back table according to the augmentation methods presented herein.

For an allograft, standard anterolateral and anteromedial arthroscopy portals are made and an incision is made on the proximal tibia for the tibial tunnel. The graft is prepared prior to performing the arthroscopy of the ACL reconstruction in some embodiments, while in other embodiments it is prepared for immediate insertion into a patient as described using the augmentation methods herein.

Figure 2:
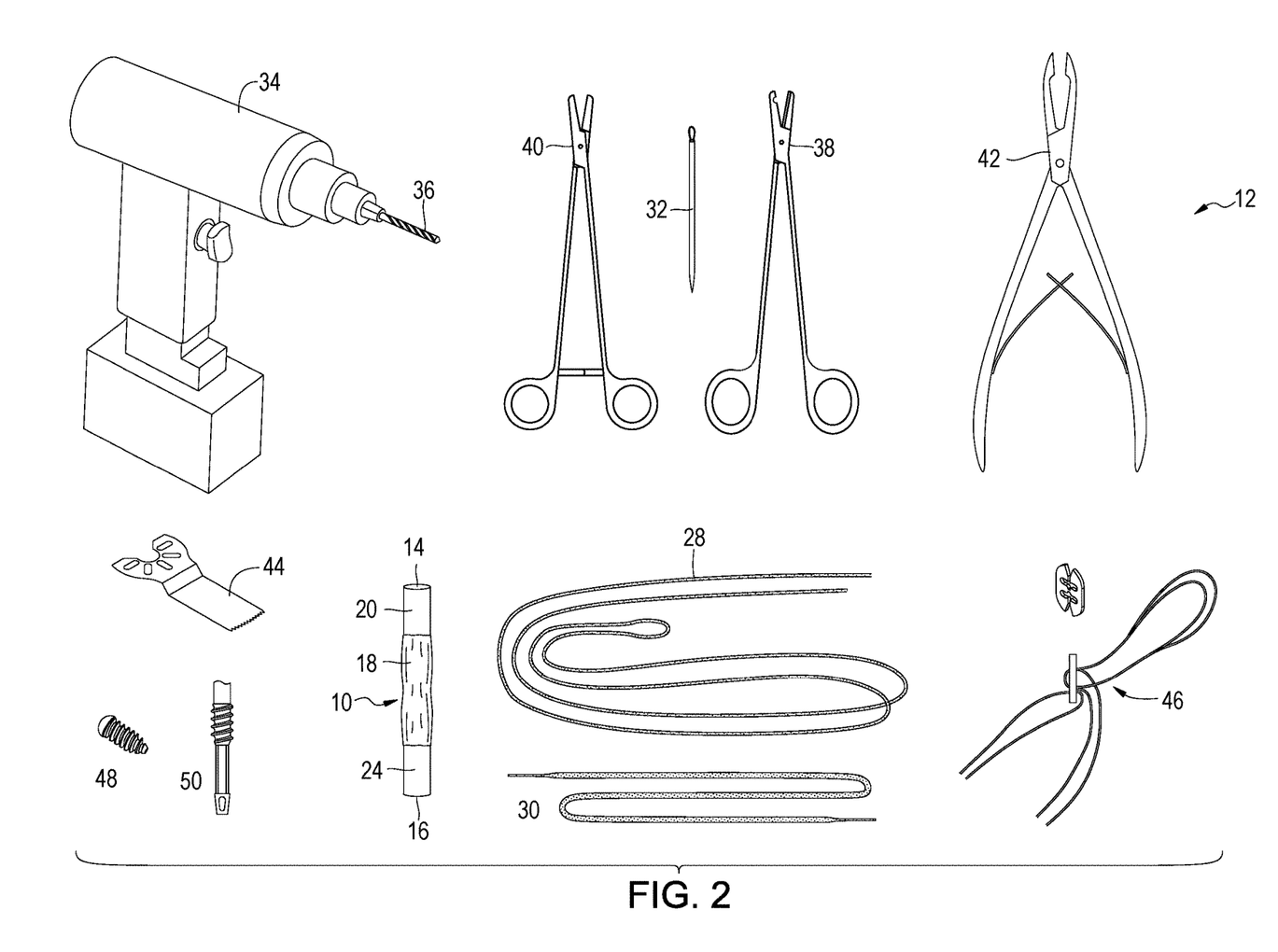
FIG. 2 is a perspective view of a surgical kit including a patellar bone-tendon graft and items for preparing the patellar bone-tendon graft for ACL reconstruction in accordance with the present invention.

Referring now to FIG. 2, a surgical kit 12 is displayed, including components for augmenting and preparing patellar tendon graft 10 for ACL reconstruction. Surgical kit 12 includes patellar tendon graft 10 with a femoral end 14, a tibial end 16, and a tendinous portion 18 between femoral end 14 and tibial end 16. Located at femoral end 14 is a femoral bone plug 20 which is to be inserted in the femur 22 of the patient. Similarly, a tibial bone plug 24 is located at tibial end 16 and is to be inserted in the tibia 26 of the patient. Also included in surgical kit 12 is at least one braided suture 28, at least one flat-braided suture 30, a straight needle 32, a drill 34, a drill bit 36, suture scissors 38, a needle driver 40, a rongeur 42, an oscillating blade 44, at least one bone-to-bone fixation suture 46, at least one interference screw 48, and at least one bone anchor 50. A subset of these components or additional components are included in surgical kit 12 in embodiments not depicted. Additional sterile coverings, personal protective equipment, power sources, and visualization equipment are contemplated for use in the present disclosure. Components of surgical kit 12 are described herein in greater detail.

Figure 3A:
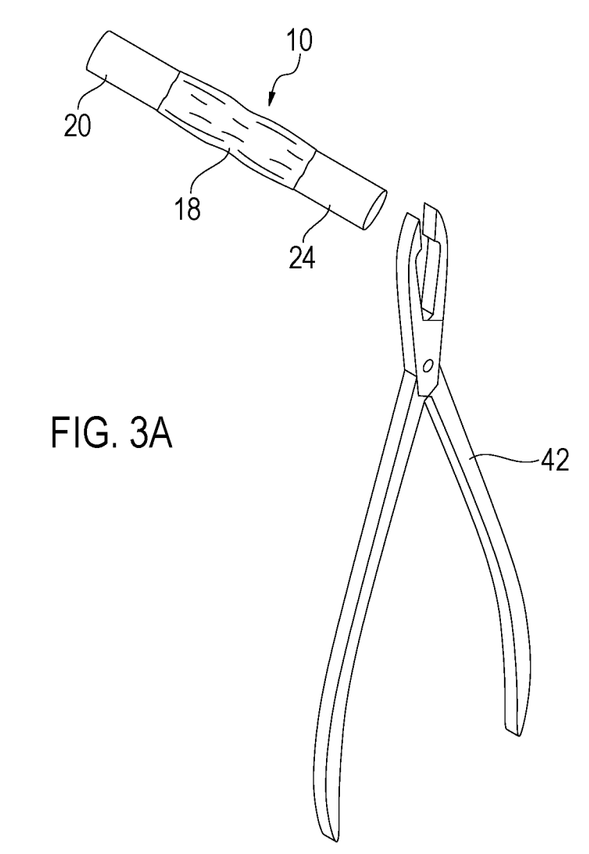
FIG. 3A is a perspective view of a patellar bone-tendon graft being shaped using a Rongeur.
Figure 3B:
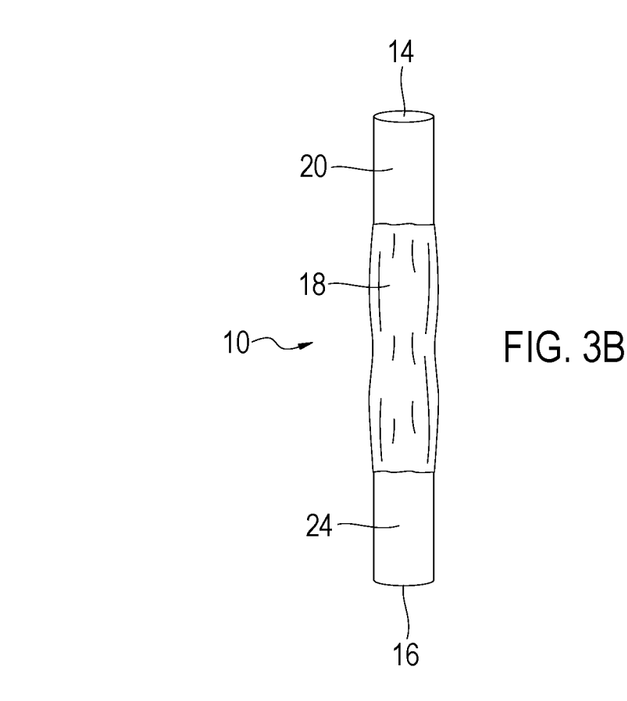
FIG. 3B is a perspective view of the patellar bone-tendon graft of FIG. 3A with shaped bone plugs.

Referring to FIGS. 3A and 3B, patellar tendon graft 10 is first prepared by shaping the bony ends of the graft in a manner known in the art. Briefly, rongeur 42 is utilized to shape femoral bone plug 20 into an approximately cylindrical shape that is approximately 10 mm in diameter and approximately 18 mm in length (FIG. 3A). Similarly, tibial bone plug 24 is shaped into approximately a cylindrical shape that is approximately 10 mm in diameter and approximately 18 mm in length (FIG. 3B). The dimensions of tibial bone plug 24 and femoral bone plug 20 vary according to patient size, bone dimensions, and desired insertion depth. Thus, other dimensions of tibial bone plug 24 and femoral bone plug 20 are possible. In some instances, an oscillating saw is additionally utilized in preparing and shaping the bony ends of patellar tendon graft 10. The oscillating saw includes oscillating blade 44, which is a 9 mm oscillating blade in some instances, and a power unit such as Stryker's Total Performance System (TPS). The preferred tendon width is typically 10 mm or 11 mm, though other widths are possible depending on patient size and application. The tendon length varied depending on application, and is approximately 35 mm to 45 mm in some embodiments.

Figure 4A:
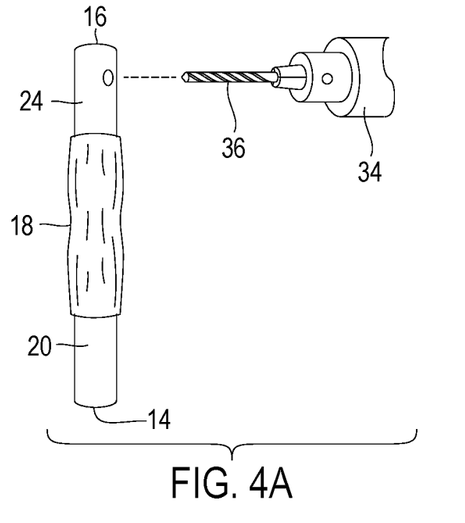
FIG. 4A depicts a medial to lateral hole being drilled in a tibial end of the bone-tendon graft of FIG. 3B.
Figure 4B:
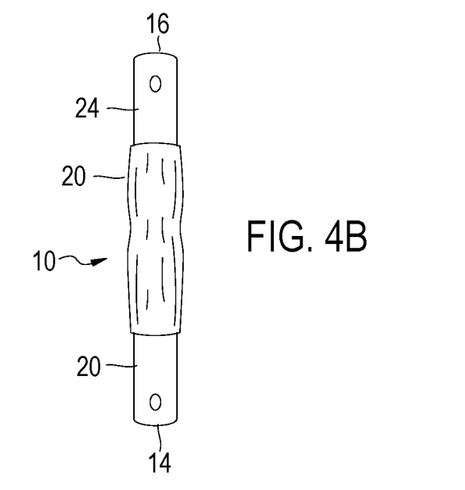
FIG. 4B depicts a medial to lateral hole drilled in a femoral end of the bone-tendon graft of FIG. 4A.

As illustrated in FIGS. 4A through 4F, drill holes are made in tibial bone plug 24 and femoral bone plug 20 and augmentation with braided suture 28 occurs. A horizontal (or medial to lateral) drill hole is made in both femoral bone plug 20 and tibial bone plug 24 (FIG. 4A). These holes are made about ⅓ of the way from the end of the bone plug (⅔ of the way from tendinous portion 18) on femoral end 14 and at the midpoint on tibial end 16 (FIG. 4B). Drill 34 with drill bit 36 are used to drill holes, and drill bit 36 is a 1.5 mm or 1.6 mm bit in the embodiments shown. However, in other embodiments drill bit 36 is larger or smaller than 1.5 mm. In yet other embodiments, the holes are different sizes and made using differently-sized drill bits. Caution is taken to avoid passing drill 34 too close to the ends of patellar bone graft 10, as it is possible to pull a suture through thin areas bone plug, especially when using an allograft.

Figure 4C:
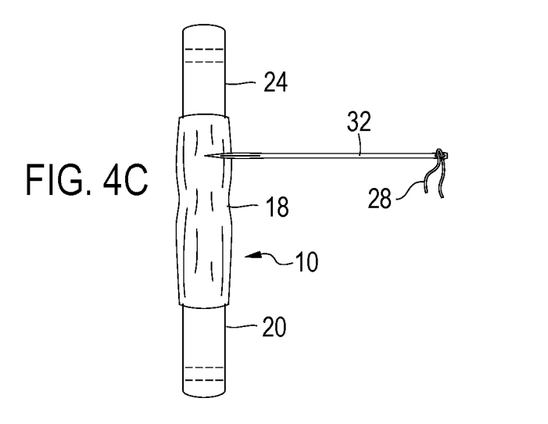
FIG. 4C depicts a braided suture being passed through a tendinous portion of the bone-tendon graft of FIG. 4B.
Figure 4D:
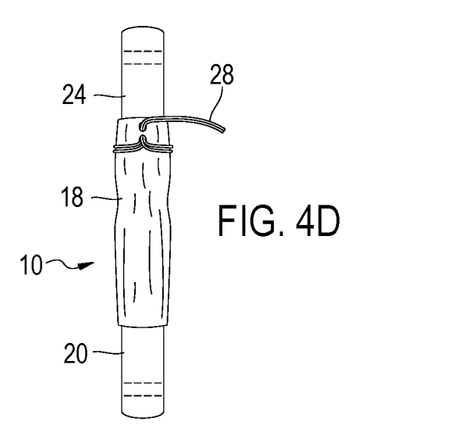
FIG. 4D depicts the braided suture wrapped around soft tissue near the tibial end of the bone-tendon graft of FIG. 4C.
Figure 4E:
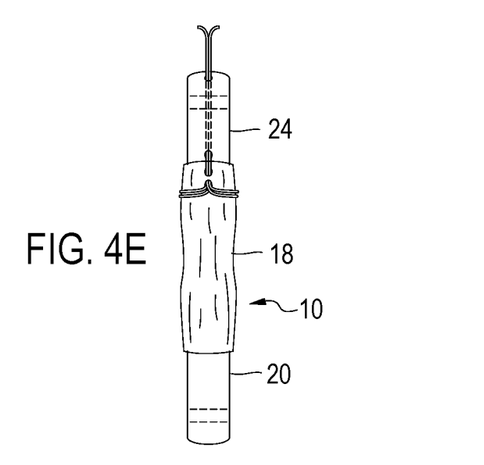
FIG. 4E depicts the braided suture exiting the tibial end of the bone-tendon graft of FIG. 4D.
Figure 4F:
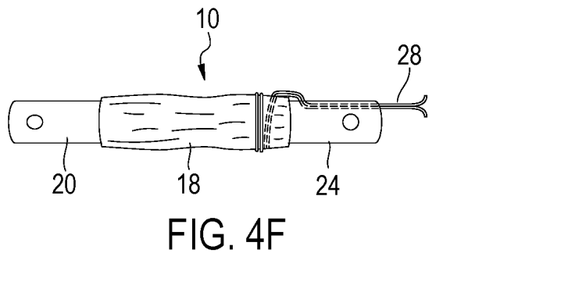
FIG. 4F depicts the braided suture exiting the tibial end of the bone-tendon graft of FIG. 4E without crossing the medial to lateral tibial hole.

As shown in FIG. 4C, braided suture 28 is passed around tendinous portion 18 near tibial end 16. Approximately 2-3 passes are made through the tendon and straight needle 32, which is in some instances a Keith needle, is then passed through the soft tissue on the posterior aspect of tibial bone plug 24 (FIG. 4D), serving as a passing or shuttle suture (FIG. 4E). Passing braided suture 28 on the backside of tibial bone plug 24 reduces its chance of being inadvertently cut by the bone tap for interference screw 48, which is used at the end of the case. In this process suture scissors 38 are available for adjustment of braided suture 28. However, cutting of braided suture 28 and not the nitinol loop on straight needle 32 should be ensured. Braided suture 28 is in some cases a FiberLoop Suture (Arthrex, Naples, Flor.). However, other braided sutures 28 are contemplated which have a small diameter, are non-absorbable, and are sterile. For instance, suture types like braided silk, braided nylon, monofilament nylon, number 5 Ticron, number 5 Ethibond, 5 mm Mersilene tape, braided ultrahigh-molecular weight polyester or polyethylene suture are compatible with the present disclosure.

Figure 5:
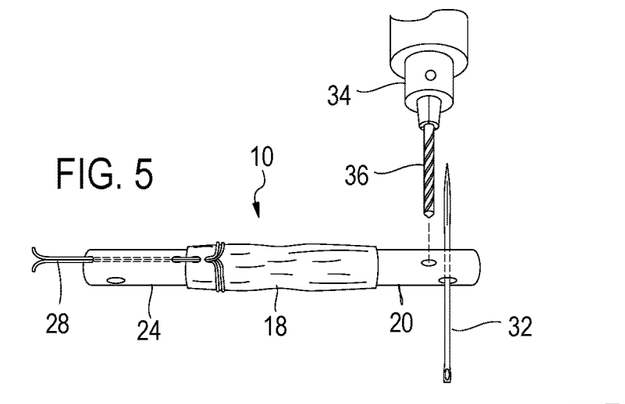
FIG. 5 an anterior to posterior hole being drilled in the femoral end of the bone-tendon graft of FIG. 4F.

Referring to FIG. 5, once braided suture 28 has been passed, it is cut and straight needle 32 is saved with the nitinol loop intact. Straight needle 32 is then placed through the horizontal drill hole in femoral bone plug 20 and maintained there as a reference. A 1.6 mm drill pass is made immediately beneath (closer to tendinous portion 18) and perpendicular (anterior to posterior) to straight needle 32 in the horizontal drill hole.

Figure 6A:
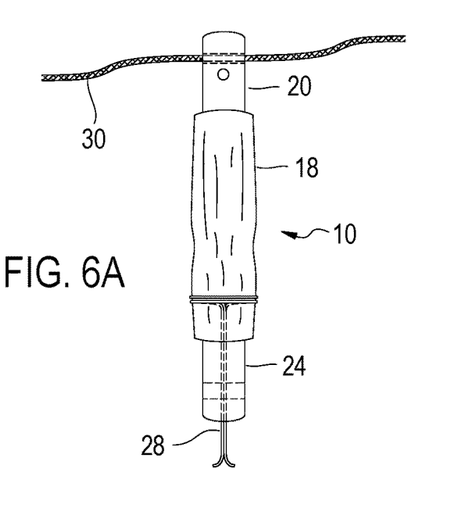
FIG. 6A depicts a flat braided suture passed through the medial to lateral femoral hole of the bone-tendon graft of FIG. 5.

Now referring to FIGS. 6A though 6G, flat-braided suture 30 is passed through patellar tendon graft 10. After the perpendicular drill hole is made, flat-braided suture 30 is passed through the horizontal hole using straight needle 32 passed as a shuttle, as shown in FIG. 6A. Flat-braided suture 30 is in some cases a FiberTape Suture (Arthrex, Naples, Flor.). However, other flat-braided sutures 30 are contemplated which have are non-absorbable and sterile. For instance, suture types like braided silk, braided nylon, monofilament nylon, number 5 Ticron, number 5 Ethibond, 5 mm Mersilene tape, braided ultrahigh-molecular weight polyester or polyethylene suture tapes are compatible with the present disclosure.

Figure 6B:
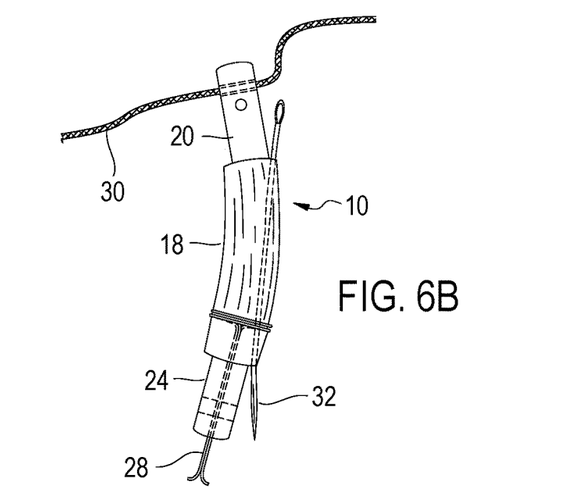
FIG. 6B depicts a bent needle being passed through the tendinous portion on a first side of the bone-tendon graft of FIG. 6A.
Figure 6C:
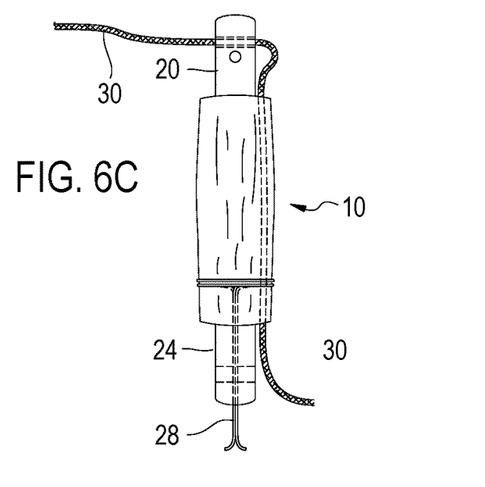
FIG. 6C depicts the flat braided suture being passed through the needle path of the tendinous portion on the first side of the bone-tendon graft of FIG. 6B.

As shown in FIG. 6B, straight needle 32 is slightly bent with needle driver 40. It is then passed through a junction of femoral bone plug 20 and tendinous portion 18 on a first side of the graft and out through a junction of tibial bone plug 24 and tendinous portion 18 on the first side of the graft, parallel to the tendon fibers. In FIG. 6C the nitinol loop on the end of straight needle 32 shuttles flat-braided suture 30 through the tendon.

Figure 6D:
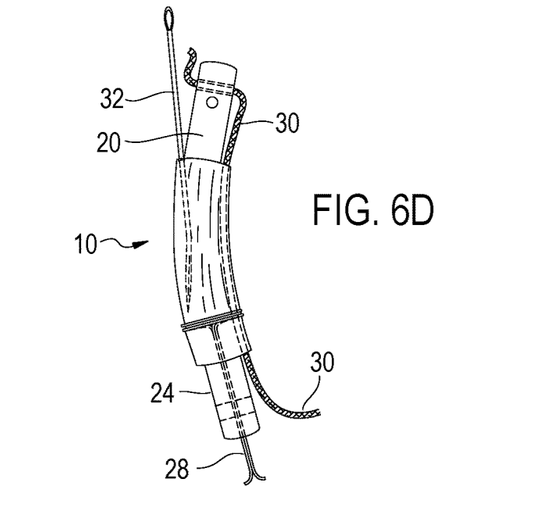
FIG. 6D depicts a bent needle being passed through the tendinous portion on a second side of the bone-tendon graft of FIG. 6C.
Figure 6E:
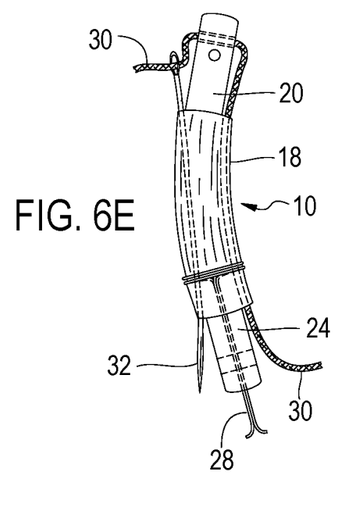
FIG. 6E depicts the flat suture being passed through the needle path of the tendinous portion on the second side of the bone-tendon graft of FIG. 6D.
Figure 6F:
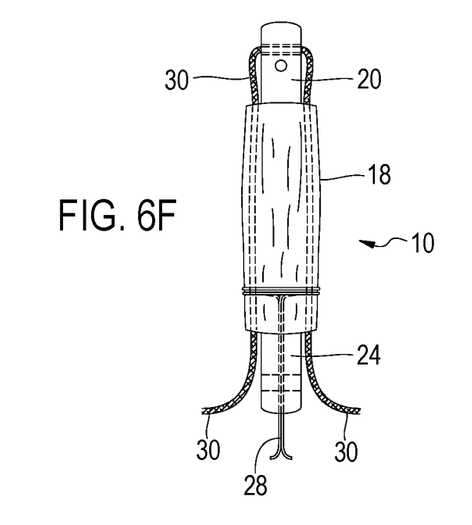
FIG. 6F depicts the flat braided suture exiting the tendinous portion on the tibial end of the tendinous portion of both sides of the bone-tendon graft of FIG. 6F.

In FIG. 6D, this step is repeated on the other side of patellar tendon graft 10 with the remaining limb of flat-braided suture 30. Straight needle 32 is passed through a junction of femoral bone plug 20 and tendinous portion 18 on a second side of the graft and out through a junction of tibial bone plug 24 and tendinous portion 18 on the second side of the graft, parallel to the tendon fibers. In FIG. 6E the nitinol loop on the end of straight needle 32 shuttles flat-braided suture 30 through the tendon on the second side. The resulting patellar tendon graft 10 includes flat-braided suture 30 running parallel to tendon fibers along the first side and second side (FIG. 6F) and with ends exiting near the junction with tibial bone plug 24 and tendinous portion 18.

Figure 6G:
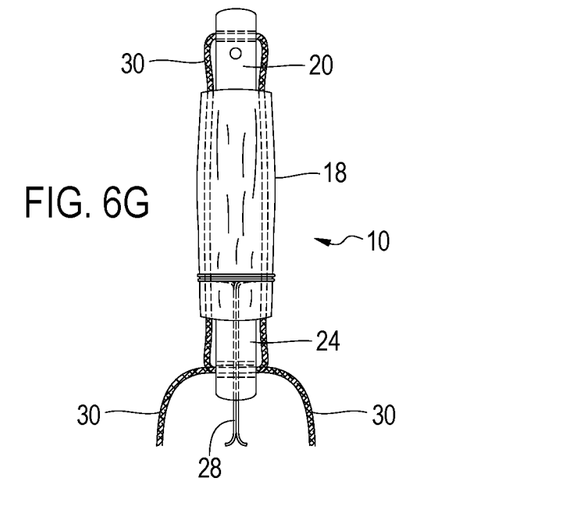
FIG. 6G. depicts the flat braided suture crisscrossing through the medial to lateral tibial hole of the bone-tendon graft of FIG. 6F.

As shown in FIG. 6G, the ends of flat-braided suture 30 are passed through the horizontal drill hole in tibial bone plug 24 in a crisscross fashion, exiting the hole on opposite sides from which they entered. Care is taken to ensure that during the crisscrossing, straight needle 32 does not pass one limb of flat-braided suture 30 through the second limb of flat-braided suture 30.

Figure 7:
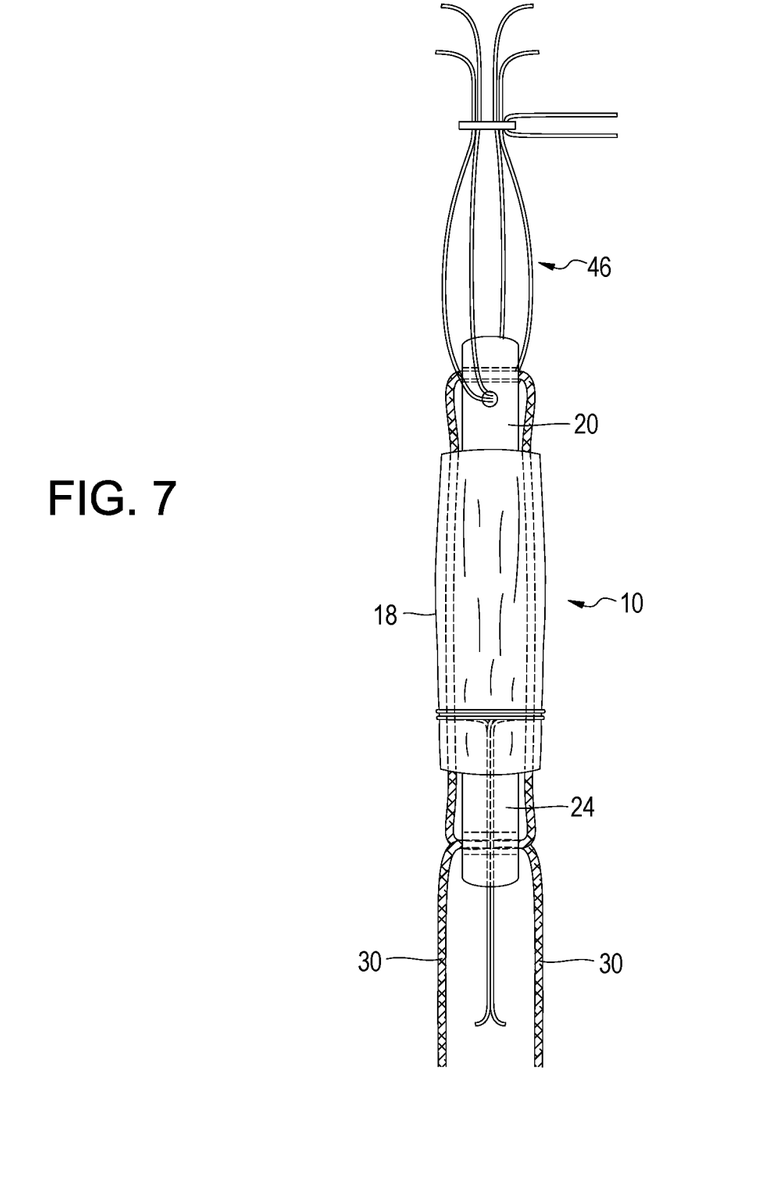
FIG. 7 depicts the bone-tendon graft of FIG. 6G with a bone-to-bone fixation suture passing through the anterior to posterior femoral hole.

Now referring to FIG. 7, bone-to-bone fixation suture 46 is passed through the anterior-to-posterior femoral drill hole, and the loop is attached to the cortical button as per the manufacturer's instructions. Bone-to-bone fixation suture 46 is in some instances a Bone-Tendon-Bone (BTB) Tightrope (Arthrex, Naples Flor.), though other bone-to-bone fixation sutures 46 are contemplated for use in the present disclosure. Briefly, a needle is used to pass bone-to-bone fixation suture 46 through anterior-to-posterior femoral drill hole and a straight section of bone-to-bone fixation suture 46 is passed through the loop. A short portion of the straight section of bone-to-bone fixation suture 46 is then placed into the suture passing loop, with the suture passing loop being pulled to deliver the straight section through the button. An interlocking loop between flat-braided suture 30 and bone-to-bone fixation suture 46 is created and patellar tendon graft 10 is ready to be implanted.

Figure 8A:
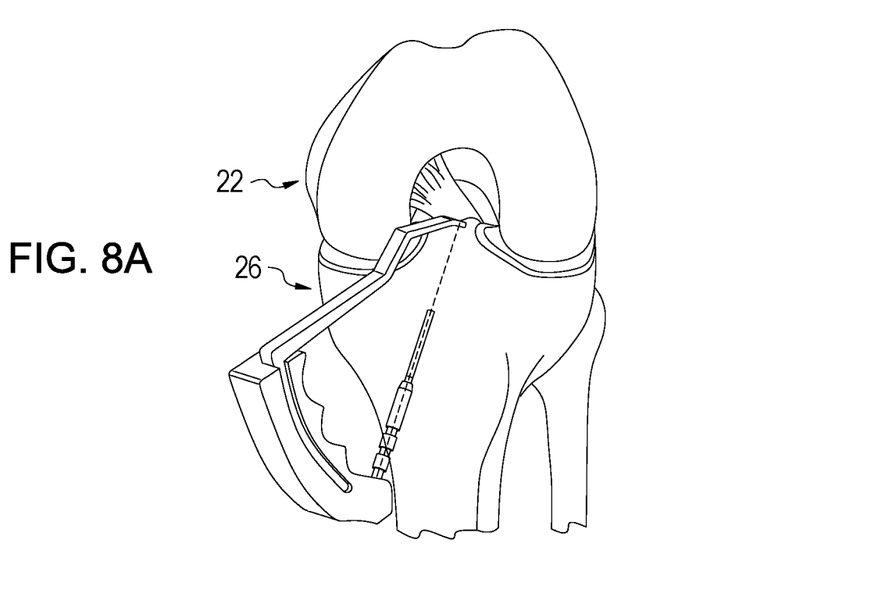
FIG. 8A depicts an initial drilling location for the tibial graft end of the patellar tendon graft for ACL reconstruction in accordance with the present invention.
Figure 8B:
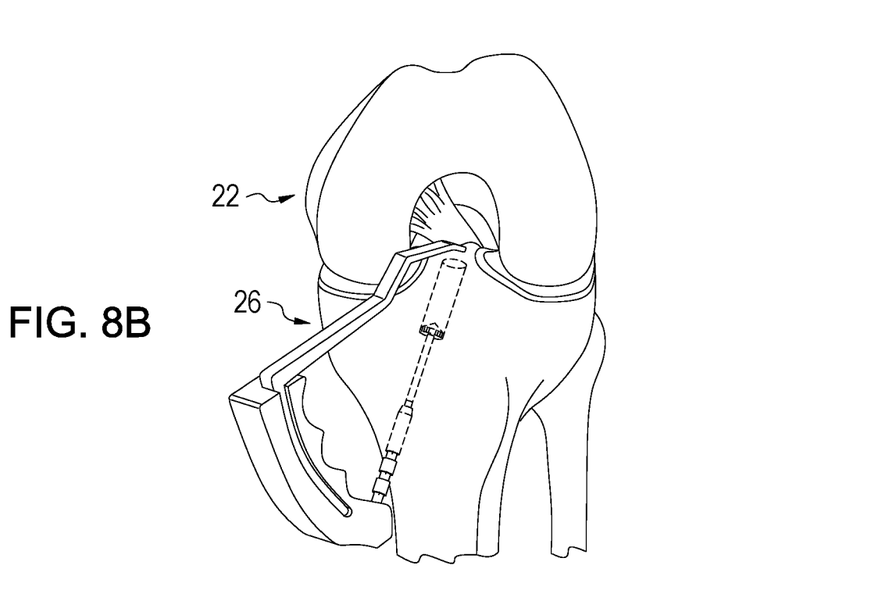
FIG. 8B shows the enlargement of the region for tibial graft end insertion for ACL reconstruction in accordance with the present invention.

In FIGS. 8A through 8F, patellar tendon graft 10 is augmented and placed in location for ACL reconstruction. An arthroscopy of the knee is performed and all compartments are examined. Any concomitant injuries are first addressed. In some instances, the ACL is debrided using a 5.0 mm arthroscopic shaver. Notchplasty is performed in cases of a narrowed, or "A-frame" type notch. Otherwise, the soft tissue is removed from the bone. Care is taken to debride back to the posterior-most aspect of the femoral condyle. A small window in the periosteum is made on the proximal anteromedial tibia 26 and the tibial drill guide is placed into the medial portal, set at 60 degrees (FIG. 8A). This allows for a long enough tunnel to provide excellent "graft-tunnel match" and ensure that no bone from tibial bone plug 24 is outside the tibial tunnel once patellar bone graft 10 is passed through and secured (FIG. 8B). A guidepin is passed through the tibial guide and into the center of the ACL insertion footprint. The guide is then removed and an approximately 11 mm reamer is passed over the guidepin. The shaver is used to remove any excess bony and soft tissue debris around the tibial tunnel that could impede passage of the graft. A rasp is used to smooth any bony spicules within the tunnel, again for ease of graft passage.

Figure 8C:
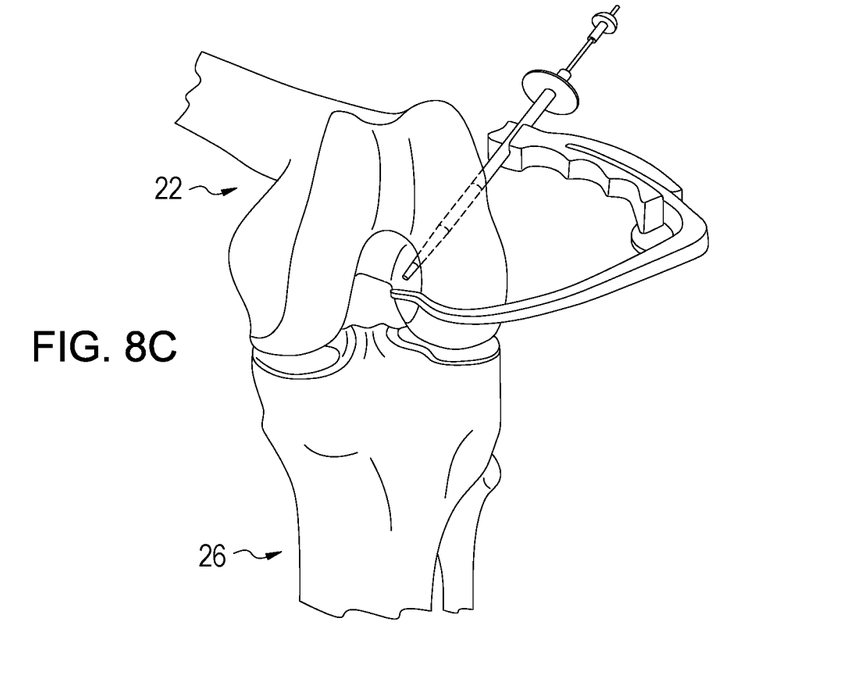
FIG. 8C depicts an initial drilling location for the femoral graft end of the patellar tendon graft for ACL reconstruction in accordance with the present invention.
Figure 8D:
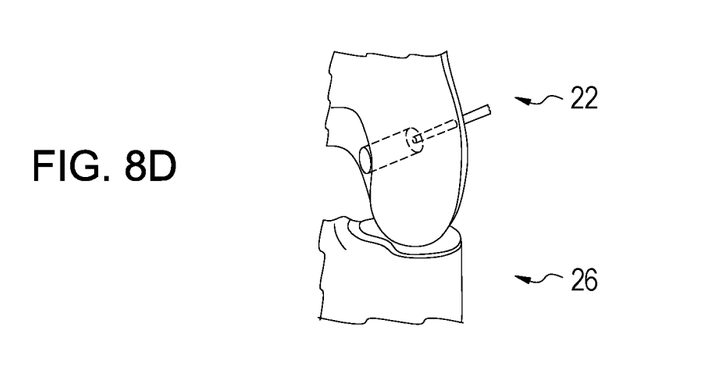
FIG. 8D shows the enlargement of the region for femoral graft end insertion for ACL reconstruction in accordance with the present invention.

The arthroscope is then transferred to the medial portal to visualize the femoral origin. As shown in FIG. 8C, a FlipCutter guide (Arthrex, Naples, Flor.) is passed through the lateral portal and placed onto the center of the ACL origin. The preferred guide has a 7 mm offset that hooks onto the posterior femoral condyle. The guide handle is elevated approximately 20 degrees from parallel to the floor and set to 105 degrees. A small incision is made with an 11 blade on the lateral side of the thigh and the drill sleeve is advanced to contact the lateral femoral cortex. The drill is passed through the lateral femur 22 and will be seen to enter the joint through the guide positioned at the femoral origin. Once the drill pass has been made, the sleeve with its 7 mm nipple are malleted into positon, engaging into the lateral femur 22. The flip mechanism is engaged and the tunnel is created by pulling back with the drill, but reaming in the forward direction (FIG. 8D). The surgeon in some instances uses one hand on the drill and use the other hand to firmly hold the drill sleeve in place. The surgeon's thumb is placed on the drill sleeve and the fingers grasp the thigh to ensure that the drill sleeve will remain in place until the tunnel has been reamed.

The FlipCutter (Arthrex, Naples, Flor.) is advanced back into the joint and the tip is flipped to allow for removal of the drill. At this point, a shaver can be placed into the tibial tunnel and into the joint for suctioning of any bony debris. The fluid should be turned off, the drill removed, and a FiberStick (Arthrex, Naples, Flor.) suture is passed through the femoral drill sleeve and into the joint. Using a loop grasper held upside down, and advanced into the tibial tunnel, the FiberStick is retrieved out of the tibial tunnel.

Figure 8E:
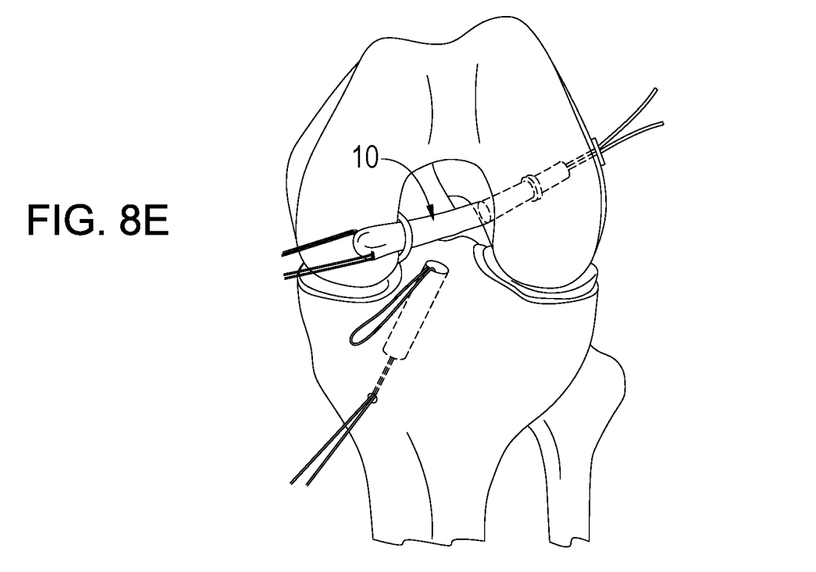
FIG. 8E depicts femoral graft end insertion and securement of patellar tendon graft for ACL reconstruction in accordance with the present invention.
Figure 8F:
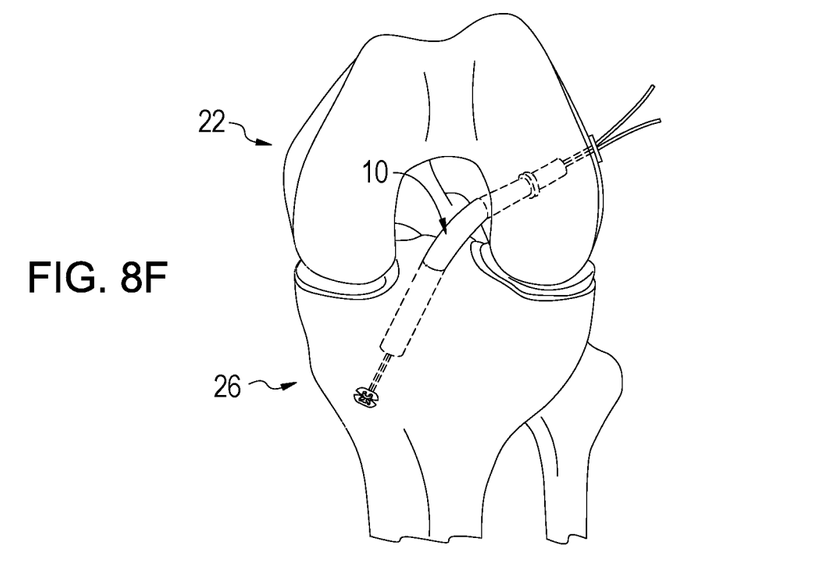
FIG. 8F depicts tibial graft end insertion and securement of patellar tendon graft for ACL reconstruction in accordance with the present invention.

The graft is then shuttled into positon and the button is secured on the lateral femoral cortex (FIG. 8E). An X-ray is used in some instances to confirm the appropriate position of the button. The white sutures of the bone-to-bone fixation suture 46 are then toggled to pull patellar tendon graft 10 into the tunnel. The femoral bone plug sometimes has to be manipulated with a probe to pass the top part of the tibial tunnel. Also, the tibial bone plug should be positioned in line with the tibial tunnel before the graft has been advanced too far.

Once patellar tendon graft 10 is securely in position (FIG. 8F), a final X-ray confirms that the button is secured against the lateral femoral cortex. A posterior drawer tension is applied to the knee and interference screw 48 is placed into the tibial tunnel. Interference screw 48 is in some instances a 10×23 mm screw, though other dimensions are possible depending on application and bone and graft dimensions. The tails of flat-braided suture 30 are then secured to tibia 26 with bone anchor 50, which is a 4.75 swivel lock anchor in some embodiments.

After the procedure, sterile dressings are applied and the patient is placed in a hinged knee brace locked in extension. The patient can weight bear as tolerated. A rehab protocol typically begins the next day with an early emphasis on motion. The patient will then progress through criteria-based phases of rehab. Return to activities are based on time for patellar tendon graft 10 to incorporated into the tunnels, ligamentization of the graft, satisfactory subjective test scores and physical exam. Finally, the patient must demonstrate return of strength and neuromuscular control with a series of video-taped movements before it is determined they are safe for return to higher level activities. This is followed by a reintegration to sport schedule with a progressive increase in activity and workload. Other criteria for rehabilitation progression are used in other instances and vary depending on the patient, injury, activity level, and other factors.

In some instances, patients are evaluated for any adverse reaction to the augmented patellar tendon graft 10 and its suture materials. Other potential areas of evaluation and observation include any negative effects of patellar tendon graft 10 and sutures on the ligamentization process that is characteristic in ACL reconstruction, biomechanical graft properties, and the potential for suture materials to overconstrain the graft, causing stress-shielding. The goals of the augmentation of patellar tendon graft 10 are to increase its mechanical load to failure, increase the rate of return to activity, reduce the chance of a repeat injury, and decrease the time to return to activity.

As will be understood by those familiar with the art, the present invention may be embodied in other specific forms without departing from the spirit or essential characteristics thereof. For instance, it is contemplated that the augmented grafts described above may be used with tendon reconstruction surgeries other than ACL reconstruction surgery including, for example, quadriceps tendon reconstruction and Achilles tendon reconstruction. Accordingly, the disclosures and descriptions herein are intended to be illustrative, but not limiting, of the scope of the invention which is set forth in the following claims.

I claim:

1. A surgical implant comprising:
   a patellar tendon graft having a femoral end, a tibial end, a tendinous portion, a femoral bone plug and a tibial bone plug, wherein the femoral bone plug is shaped into a first cylinder and the tibial bone plug is shaped into a second cylinder;
   a medial to lateral drill hole formed in each of the femoral bone plug and the tibial bone plug;
   a braided suture secured to the patellar tendon graft, the braided suture passed round the tendinous portion of the patellar tendon graft, passed through the tendinous portion, and passed through soft tissue on a posterior portion of the tibial bone plug and out through the tibial end of the patellar tendon graft;
   an anterior to posterior hole formed in the femoral bone plug immediately beneath the medial to lateral drill hole therein;
   a flat-braided suture passed through the medial to lateral hole of the femoral bone plug, wherein a first end of the flat-braided suture is passed through a junction of the femoral bone plug and the tendinous portion and out through a junction of the tibial bone plug and the tendinous portion, wherein a second end of the flat-braided suture is passed through the junction of the femoral bone plug and the tendinous portion and out through the junction of the tibial bone plug and the tendinous portion, and wherein the first end of the flat-braided suture and the second end of the flat-braided suture are further passed through the medial to lateral drill hole in the tibial bone plug in a crisscross fashion; and
   a bone to bone fixation suture assembly passed through the anterior to posterior hole in the femoral bone plug and operatively coupled to the patellar tendon graft thereby forming an interlocking loop between the flat-braided suture and the bone to bone fixation suture assembly.

2. A surgical kit including the surgical implant of claim 1 and at least one interference screw and at least one bone anchor.

3. The surgical kit of claim 2, further including a sterile package in which the surgical implant, the at least one interference screw and the at least one bone anchor are stored, the sterile package being selected from the group consisting of a sealed tray, a sealed bag, a sealed metal foil bag, a sealed plastic bag, a sealed plastic tray, a sealed metal tray, and a metal foil-sealed plastic or metal tray.

\* \* \* \* \*